(12) United States Patent
Niimi et al.

(10) Patent No.: US 12,360,023 B2
(45) Date of Patent: Jul. 15, 2025

(54) METHOD OF PRETREATING BLOOD SAMPLE

(71) Applicant: LABTECHS Inc., Toyama (JP)

(72) Inventors: Hideki Niimi, Toyama (JP); Kazushige Sugie, Toyama (JP); Isao Kitajima, Toyama (JP); Tomohiro Ueno, Toyama (JP); Atsushi Matsui, Toyama (JP)

(73) Assignee: National University Corporation University of Toyama (JP)

( * ) Notice: Subject to any disclaimer, the term of this patent is extended or adjusted under 35 U.S.C. 154(b) by 0 days.

(21) Appl. No.: 16/874,008

(22) Filed: May 14, 2020

(65) Prior Publication Data
US 2020/0355588 A1 Nov. 12, 2020

Related U.S. Application Data

(63) Continuation of application No. PCT/JP2018/023388, filed on Jun. 20, 2018.

(30) Foreign Application Priority Data

Nov. 15, 2017 (JP) ................................. 2017-219547

(51) Int. Cl.
*G01N 1/40* (2006.01)
*C12Q 1/00* (2006.01)

(52) U.S. Cl.
CPC ........... *G01N 1/4044* (2013.01); *C12Q 1/008* (2013.01)

(58) Field of Classification Search
CPC .............................. G01N 1/4044; C12Q 1/008
USPC .......................................................... 435/18
See application file for complete search history.

(56) References Cited

U.S. PATENT DOCUMENTS

| 3,745,090 | A | * | 7/1973 | Chappelle et al. ...... | C12Q 1/06 435/8 |
| 2004/0185437 | A1 | * | 9/2004 | Hermet ................ | G01N 1/4077 435/5 |
| 2011/0076706 | A1 | * | 3/2011 | Fleming ................ | C12Q 1/008 435/8 |

FOREIGN PATENT DOCUMENTS

JP 2014-235076 A 12/2014
WO WO 2017/042819 * 3/2017

OTHER PUBLICATIONS

Wikipedia, Proteinase K, Accessed Sep. 10, 2021, Available online at: en.wikipedia.org/wiki/ Proteinase_K.*
Hattori et al., "Novel Antibiotic Susceptibility Tests by the ATP-Bioluminescence Method Using Filamentous Cell Treatment", Antimicrobial Agents and Chemotherapy, vol. 42, pp. 1406-1411, 1998.
Sugie. et al., "A Novel Procedure for Measuring Viable Bacterial ATP in Septic Blood with Minimal ATP Background of Human Origin" posted to https://toyama.repo.nii.ac.jp/ on Jun. 22, 2017 (14 pages, including partial translation).

* cited by examiner

*Primary Examiner* — Jennifer M. H. Tichy
(74) *Attorney, Agent, or Firm* — Harness, Dickey & Pierce, P.L.C.

(57) ABSTRACT

A method of pretreating a blood sample for measuring ATP of a pathogenic microorganism in blood, comprising: preparing a pellet of platelets and the pathogenic microorganism from the blood sample; and subjecting the pellet of platelets and the pathogenic microorganism to the following steps (A) to (C) in any order (including multiple simultaneous steps). A method of pretreating a cultured blood sample, wherein the method is a simplified method, does not comprise the following step (A), and comprises the steps (B) and (C) only simultaneously performed. (A) digesting cell membrane proteins of the platelets with a protease; (B) swelling the platelets in a hypotonic solution; and (C) disrupting cell membranes of the platelets with a detergent solution under a condition of suppressing an effect on the pathogenic microorganism.

4 Claims, 14 Drawing Sheets

FIG. 1
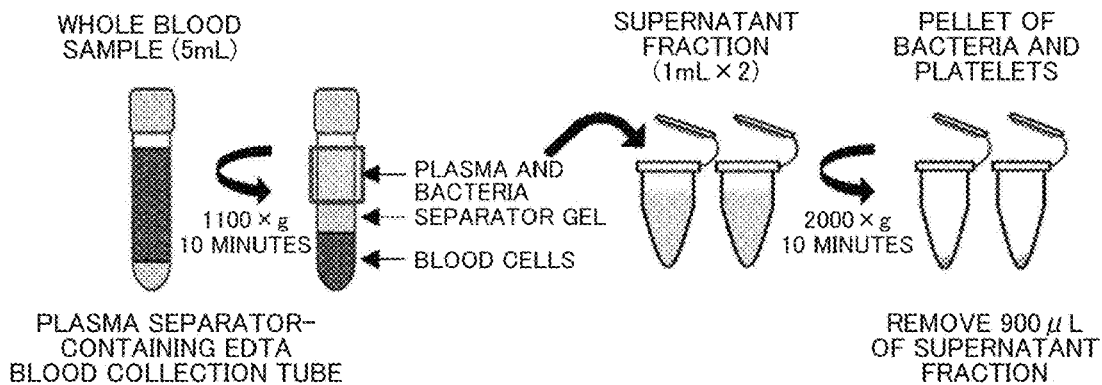
FIG. 2
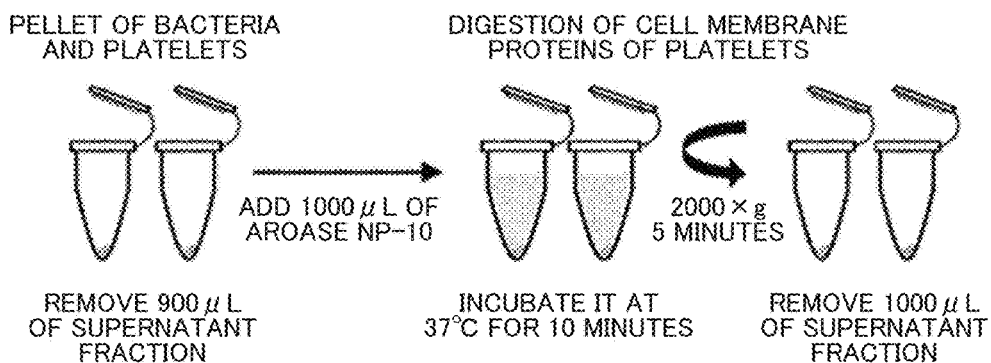
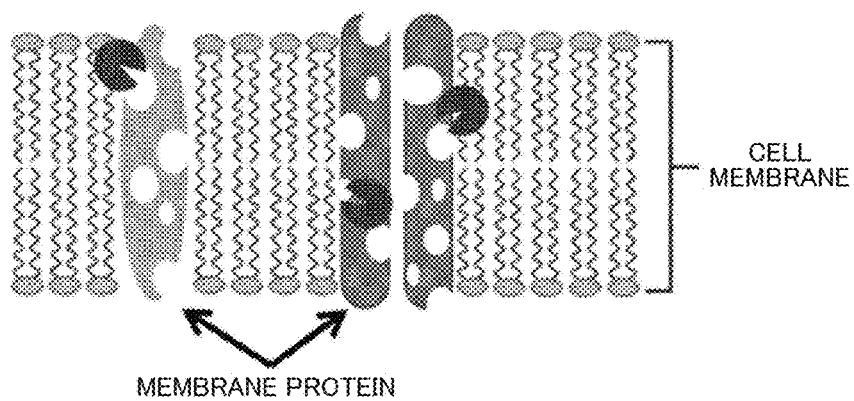

FIG. 3
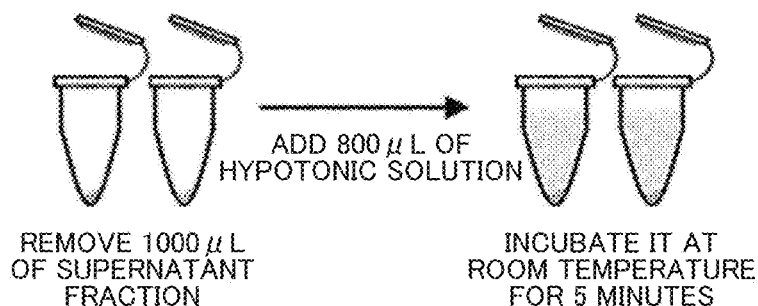
CELL SWELLING CAUSED BY TREATMENT WITH HYPOTONIC SOLUTION
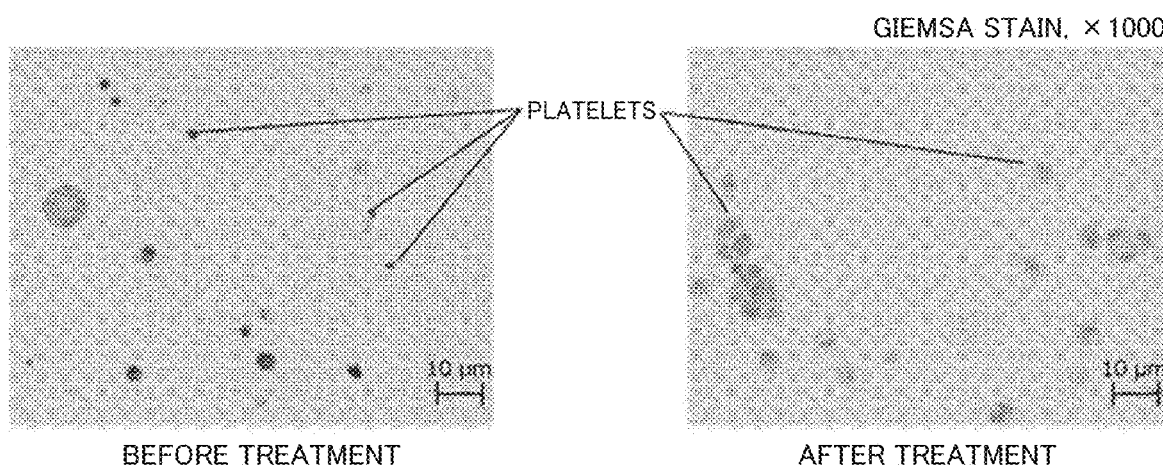
AFTER TREATMENT WITH HYPOTONIC SOLUTION, BLOOD CELLS ARE SWOLLEN AND EASILY DISRUPTED

ALL BLOOD CELLS WERE DISRUPTED AFTER TREATMENT

ATP IN PRE-AND POST-TREATMENT BLOODS
FROM HEALTHY VOLUNTEERS WAS COMPARED
→VALUES WERE LOWERED TO
ABOUT 1/2,500,000 AFTER TREATMENT

FIG. 9

TABLE 1

| BACTERIAL SPECIES | SAMPLE PRE-TREATMENT | ATP MEASUREMENT THROUGH BIOLUMINESCENCE | | | | MEASUREMENT OF COLONY FORMING UNIT (CFU) | | | |
|---|---|---|---|---|---|---|---|---|---|
| | | AVERAGE OF THREE MEASUREMENTS | SD | CV (%) | RECOVERY RATE(%) | AVERAGE OF THREE MEASUREMENTS | SD | CV (%) | RECOVERY RATE(%) |
| Acinetobacter sp. | BEFORE TREATMENT | 14481.1 | 329.5 | 2.3 | 130.7 | 18933.3 | 1798.8 | 9.5 | 127.6 |
| | AFTER TREATMENT | 18923.9 | 1956.0 | 10.3 | | 24133.3 | 377.1 | 1.6 | |
| Aeromonas hydrophila | BEFORE TREATMENT | 26553.8 | 2458.5 | 9.3 | 49.2 | 70800.0 | 11293.8 | 16.0 | 23.4 |
| | AFTER TREATMENT | 13056.6 | 416.9 | 3.2 | | 16533.3 | 4446.2 | 26.9 | |
| Bacillus cereus | BEFORE TREATMENT | 55402.7 | 4174.1 | 7.5 | 22.9 | 8266.7 | 1611.1 | 19.5 | 66.1 |
| | AFTER TREATMENT | 12670.0 | 803.2 | 6.3 | | 5466.7 | 678.9 | 12.4 | |
| Chryseobacterium sp. | BEFORE TREATMENT | 34446.0 | 2424.9 | 7.0 | 71.1 | 60800.0 | 6203.4 | 10.2 | 105.3 |
| | AFTER TREATMENT | 83679.0 | 10842.4 | 13.0 | | 64000.0 | 3919.2 | 6.1 | |
| Citrobacter freundii | BEFORE TREATMENT | 63246.1 | 3660.8 | 5.8 | 132.2 | 103800.0 | 8769.6 | 8.5 | 55.7 |
| | AFTER TREATMENT | 83679.0 | 10842.4 | 13.0 | | 57733.3 | 13154.8 | 22.8 | |
| Corynebacterium sp. | BEFORE TREATMENT | 43471.3 | 4323.9 | 9.9 | 36.9 | 55066.7 | 7165.3 | 13.0 | 43.3 |
| | AFTER TREATMENT | 16044.7 | 388.6 | 2.4 | | 23866.7 | 5239.2 | 22.0 | |
| Enterobacter cloacae | BEFORE TREATMENT | 33160.3 | 1552.0 | 4.7 | 112.1 | 48000.0 | 6605.0 | 13.8 | 80.6 |
| | AFTER TREATMENT | 37177.5 | 2750.4 | 7.4 | | 38800.0 | 7382.9 | 19.0 | |
| Enterococcus faecium | BEFORE TREATMENT | 53923.1 | 8414.6 | 15.6 | 73.8 | 24533.3 | 1611.1 | 6.6 | 91.8 |
| | AFTER TREATMENT | 39780.1 | 1837.7 | 4.6 | | 22533.3 | 1798.8 | 8.0 | |
| Escherichia coli | BEFORE TREATMENT | 65458.3 | 4172.4 | 6.6 | 167.3 | 110400.0 | 7353.8 | 6.7 | 80.1 |
| | AFTER TREATMENT | 106142.9 | 3827.1 | 3.6 | | 88400.0 | 24967.2 | 28.2 | |
| Klebsiella pneumoniae | BEFORE TREATMENT | 38431.7 | 1636.7 | 4.3 | 155.4 | 52933.3 | 10640.0 | 20.1 | 76.1 |
| | AFTER TREATMENT | 59709.6 | 966.6 | 1.6 | | 40266.7 | 10619.9 | 26.4 | |
| Listeria monocytogenes | BEFORE TREATMENT | 62980.4 | 965.7 | 1.5 | 64.2 | 211866.7 | 3582.7 | 1.7 | 44.2 |
| | AFTER TREATMENT | 40440.6 | 1481.6 | 3.7 | | 93733.3 | 4434.2 | 4.7 | |
| Morganella morganii | BEFORE TREATMENT | 35793.7 | 2938.3 | 8.2 | 101.3 | 137866.7 | 18481.9 | 13.4 | 80.7 |
| | AFTER TREATMENT | 36257.8 | 7154.7 | 19.7 | | 111200.0 | 5995.6 | 5.4 | |
| Neisseria sp. | BEFORE TREATMENT | 38346.9 | 4981.8 | 13.0 | 59.8 | 90266.6 | 22992.3 | 25.5 | 26.0 |
| | AFTER TREATMENT | 22920.5 | 1045.0 | 4.6 | | 23466.6 | 4349.2 | 18.5 | |
| Proteus mirabilis | BEFORE TREATMENT | 37317.0 | 2571.1 | 6.9 | 98.2 | 140666.7 | 12633.6 | 9.0 | 39.7 |
| | AFTER TREATMENT | 36646.2 | 1874.4 | 5.1 | | 55866.7 | 20192.0 | 36.1 | |
| Pseudomonas aeruginosa | BEFORE TREATMENT | 25475.1 | 873.3 | 3.4 | 95.0 | 60400.0 | 9403.5 | 15.6 | 120.5 |
| | AFTER TREATMENT | 24211.6 | 950.2 | 3.9 | | 72800.0 | 11482.2 | 15.8 | |
| Serratia marcescens | BEFORE TREATMENT | 8946.6 | 1404.6 | 15.9 | 146.6 | 29600.0 | 6101.1 | 20.6 | 87.8 |
| | AFTER TREATMENT | 12971.7 | 1813.8 | 14.0 | | 26000.0 | 4079.2 | 15.7 | |
| Staphylococcus aureus | BEFORE TREATMENT | 26039.0 | 1015.6 | 3.9 | 88.1 | 115733.3 | 4736.6 | 4.1 | 74.2 |
| | AFTER TREATMENT | 22928.9 | 800.9 | 3.5 | | 85866.7 | 2719.5 | 3.2 | |
| Stenotrophomonas maltophilia | BEFORE TREATMENT | 4326.3 | 576.5 | 13.3 | 69.4 | 48400.0 | 2902.9 | 6.0 | 62.3 |
| | AFTER TREATMENT | 3003.3 | 221.5 | 7.4 | | 30133.3 | 7514.1 | 24.9 | |
| Streptococcus agalactiae | BEFORE TREATMENT | 41693.6 | 2475.0 | 5.9 | 104.7 | 27366.7 | 1795.3 | 6.5 | 80.1 |
| | AFTER TREATMENT | 43632.9 | 1892.7 | 4.3 | | 22000.0 | 3456.4 | 15.7 | |
| AVERAGE RECOVERY RATE OF VIABLE MICROORGANISMS (19 BACTERIAL SPECIES) AFTER PRETREATMENT | | | | | 93.6 | | | | 71.9 |

FIG. 12

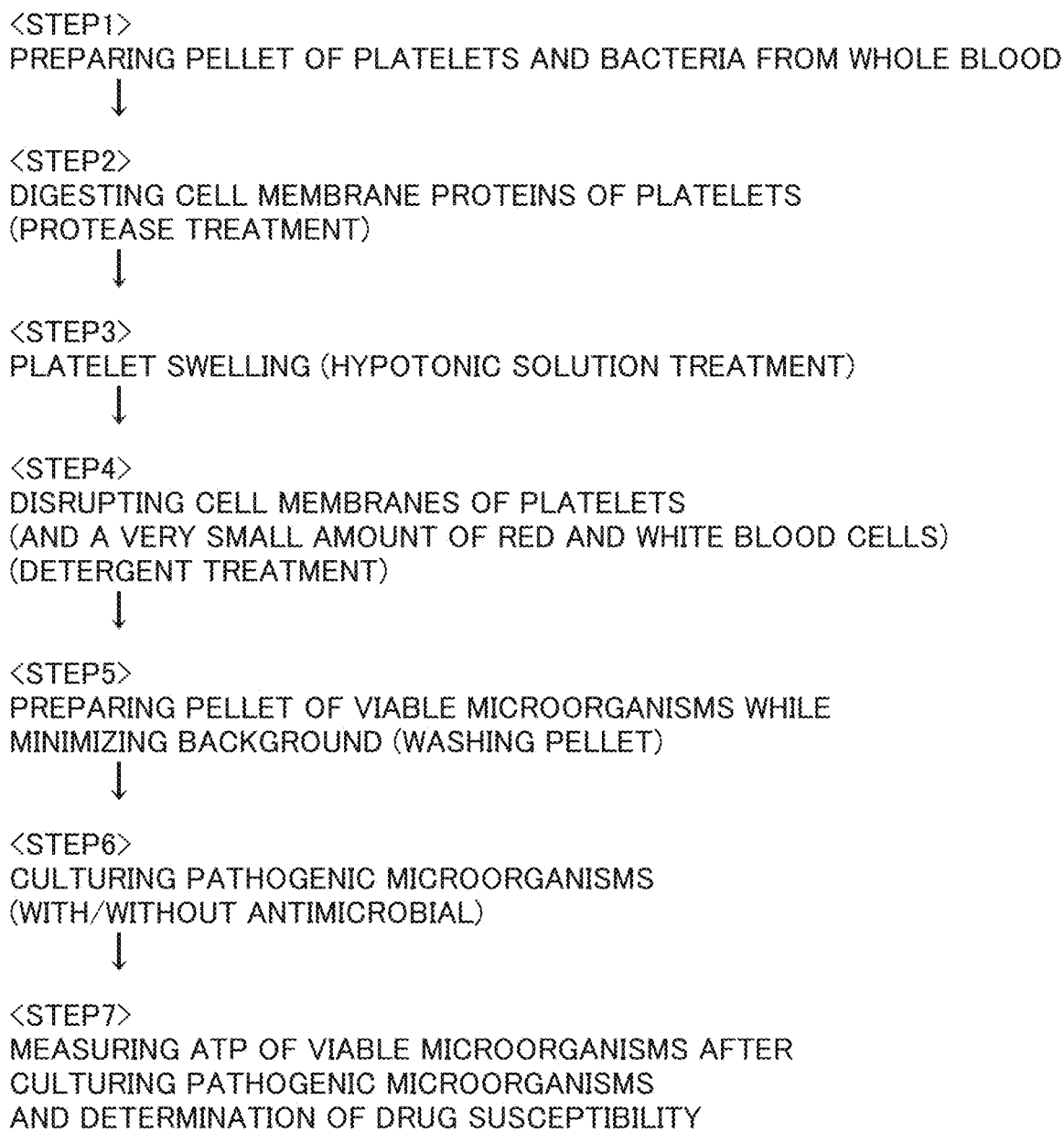

PROCEDURE OF SAMPLE PRETREATMENT (BAMP PROCEDURE)
AND ATP MEASUREMENT

<STEP1>
PREPARING PELLET OF PLATELETS AND BACTERIA FROM WHOLE BLOOD
↓

<STEP2>
DIGESTING CELL MEMBRANE PROTEINS OF PLATELETS
(PROTEASE TREATMENT)
↓

<STEP3>
PLATELET SWELLING (HYPOTONIC SOLUTION TREATMENT)
↓

<STEP4>
DISRUPTING CELL MEMBRANES OF PLATELETS
(AND A VERY SMALL AMOUNT OF RED AND WHITE BLOOD CELLS)
(DETERGENT TREATMENT)
↓

<STEP5>
PREPARING PELLET OF VIABLE MICROORGANISMS WHILE
MINIMIZING BACKGROUND (WASHING PELLET)
↓

<STEP6>
CULTURING PATHOGENIC MICROORGANISMS
(WITH/WITHOUT ANTIMICROBIAL)
↓

<STEP7>
MEASURING ATP OF VIABLE MICROORGANISMS AFTER
CULTURING PATHOGENIC MICROORGANISMS
AND DETERMINATION OF DRUG SUSCEPTIBILITY

FIG. 13

TABLE 2

| EXPERIMENT OF MEASURING ATP BACKGROUND | CULTURING 10 ML OF BLOOD FROM HEALTHY SUBJECTS FOR 4 HOURS → SUBJECTING 100 μL OF SUPERNATANT TO SIMPLIFIED PROTOCOL → CULTURING IT FOR 1 HOUR → MEASURING ATP | | |
|---|---|---|---|
| STEP OF DISRUPTING BLOOD CELLS | HYPOTONIC SOLUTION +Detergent A | HYPOTONIC SOLUTION +0.05% SDS (WITHOUT SAPONIN) | HYPOTONIC SOLUTION ONLY |
| 1ST ATP MEASUREMENT | 334.8 | 13,544.1 | 204,799.1 |
| 2ND ATP MEASUREMENT | 337.1 | 16,055.6 | 176,298.5 |
| 3RD ATP MEASUREMENT | 407.5 | 14,072.3 | 195,984.9 |
| AVERAGE OF ATP MEASUREMENTS(CPS) | 359.8 | 14,557.3 | 192,360.8 |

FIG. 15

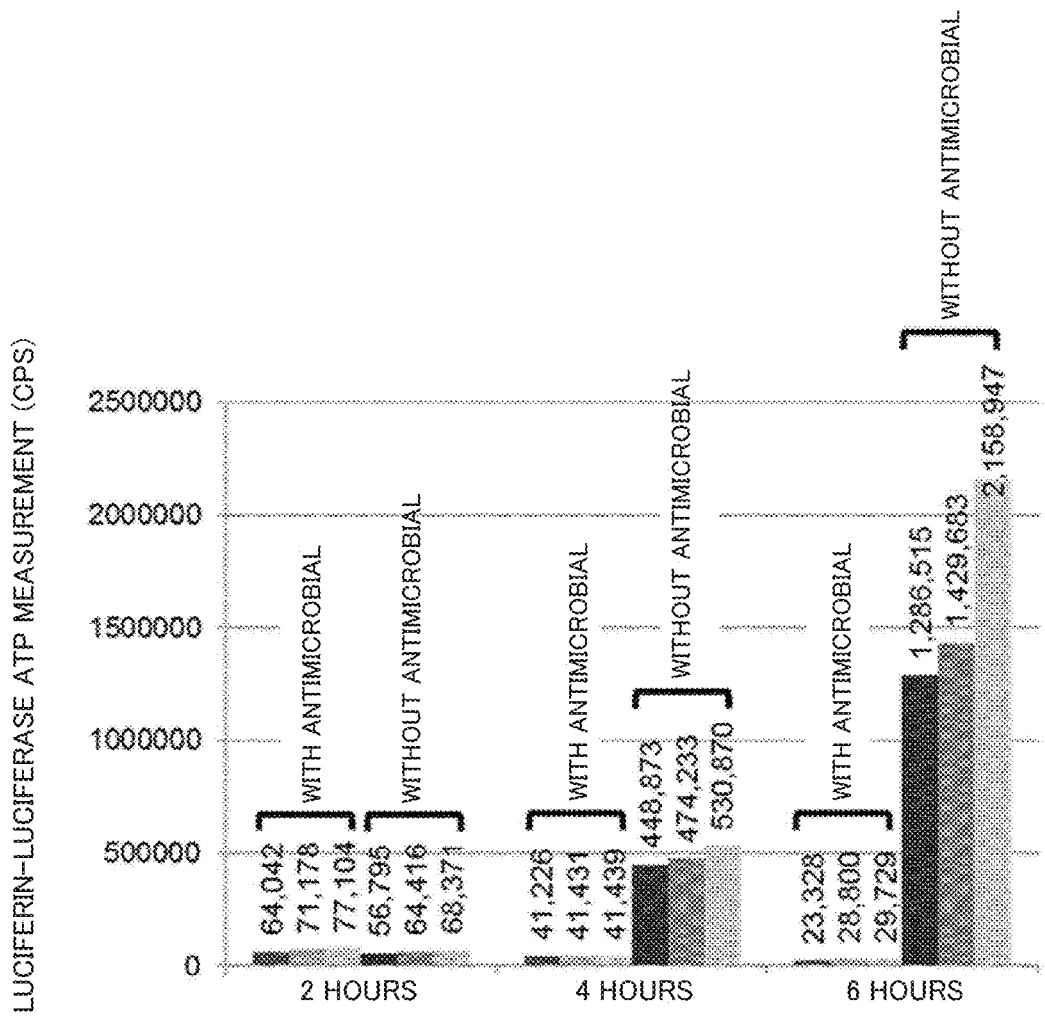

| CULTURE TIME | 2 HOURS | 4 HOURS | 6 HOURS | DETERMINA-TION RESULT |
|---|---|---|---|---|
| WITHOUT ANTIMICROBIAL (LVFX): ATP AVERAGE | 63,194 | 484,659 | 1,6251,048 | LVFX-SUSCEPTIBLE |
| WITH ANTIMICROBIAL (LVFX): ATP AVERAGE | 70,775 | 41,365 | 27,286 | |

*RESULTS OF IDENTIFICATION OF PATHOGENIC MICROORGANISMS THROUGH CONVENTIONAL METHOD (BLOOD CULTURE + WALKAWAY), AND DRUG SUSCEPTIBILITY

DETECTED MICROORGANISM: Streptococcus anginosus
DRUG SUSCEPTIBILITY: ANTIMICROBIAL (LEVOFLOXACIN: LVFX) SUSCEPTIBLE

METHOD OF PRETREATING BLOOD SAMPLE

CROSS REFERENCE TO RELATED APPLICATION

This application is a continuation of International Patent Application No. PCT/JP2018/023388, having an international filing date of Jun. 20, 2018, which designated the United States, the entirety of which is incorporated herein by reference. Japanese Patent Application No. 2017-219547 filed on Nov. 15, 2017 is also incorporated herein by reference in its entirety.

BACKGROUND OF THE DISCLOSURE

Field of the Disclosure

The present disclosure relates to a method of pretreating a blood sample for measuring adenosine triphosphate (ATP) of pathogenic microorganisms while minimizing human-derived ATP, for example, when pathogenic microorganisms responsible for infections such as sepsis are directly recovered in a viable state from a sample or when pathogenic microorganisms are directly recovered from a blood culture bottle (cultured blood sample).

Description of the Related Art

All living organisms use adenosine triphosphate (ATP) as energy to perform life activities. Therefore, if human-derived ATP in blood can be removed and minimized, and pathogenic microorganisms responsible for sepsis or other infections can be recovered in a viable state, determination of the presence or absence of viable microorganisms (pathogenic microorganisms) and drug susceptibility tests can be performed through ATP measurement.

Since current drug susceptibility tests are determined based on the turbidity of microorganisms, it is necessary to first separate and culture pathogenic microorganisms, and then wait for sufficient growth of the microorganisms in the drug susceptibility test. Thus, the tests typically require 2 to 3 days from the blood collection.

In contrast, it has been reported that measurement of ATP produced by microorganisms accelerates drug susceptibility tests starting from bacterial colonies (Hattori N. et al. Novel antibiotic susceptibility tests by the ATP-bioluminescence method using filamentous cell treatment. Antimicrobial Agents and Chemotherapy: 42, 1406-1411, 1998).

This report describes that a conventional method starting from bacterial colonies requires 18 to 24 hours whereas ATP measurement allows the determination in approximately 6 hours.

However, the above method starts from colonies and requires 1 to 2 days for separation culture before obtaining the colonies, and therefore the time from blood collection is not necessarily short.

JP-A-2014-235076 describes that, for example, blood cells were disrupted with a detergent solution consisting of 0.1 or 0.2 wt % sodium dodecyl sulfate (SDS) and 2 wt % saponin.

However, when SDS concentration is high, such as 0.1% or 0.2%, *Streptococcus agalactiae*, which is often detected as a pathogenic microorganism responsible for, for example, sepsis, was largely killed and unable to be recovered in a viable state.

Conversely, when SDS concentration is lowered to 0.05%, the recovery rate of viable microorganisms increased. However, most platelets in blood were not disrupted, leading to failure of minimization of human-derived ATP and detection of viable microorganisms through ATP measurement.

BRIEF DESCRIPTION OF THE DRAWINGS

FIG. 1 illustrates operations to prepare pellets of platelets and pathogenic microorganisms from a blood sample;

FIG. 2 illustrates operations and an effect of protease treatment;

FIG. 3 illustrates operations of hypotonic solution treatment and photographs of cell swelling;

FIG. 8A represents photomicrographs, and FIG. 8B illustrates results of ATP measurement;

FIG. 9 illustrates results of evaluating an ability to recover microorganisms;

FIG. 12 illustrates a procedure of sample pretreatment (BAMB Procedure) and ATP measurement;

FIG. 13 illustrates results of measuring ATP background in cultured blood samples according to simplified pretreatment protocols different in steps of disrupting blood cells;

FIG. 15 illustrates an example of determining drug susceptibility of cultured blood samples.

DETAILED DESCRIPTION OF THE PREFERRED EMBODIMENTS

Figure 4:
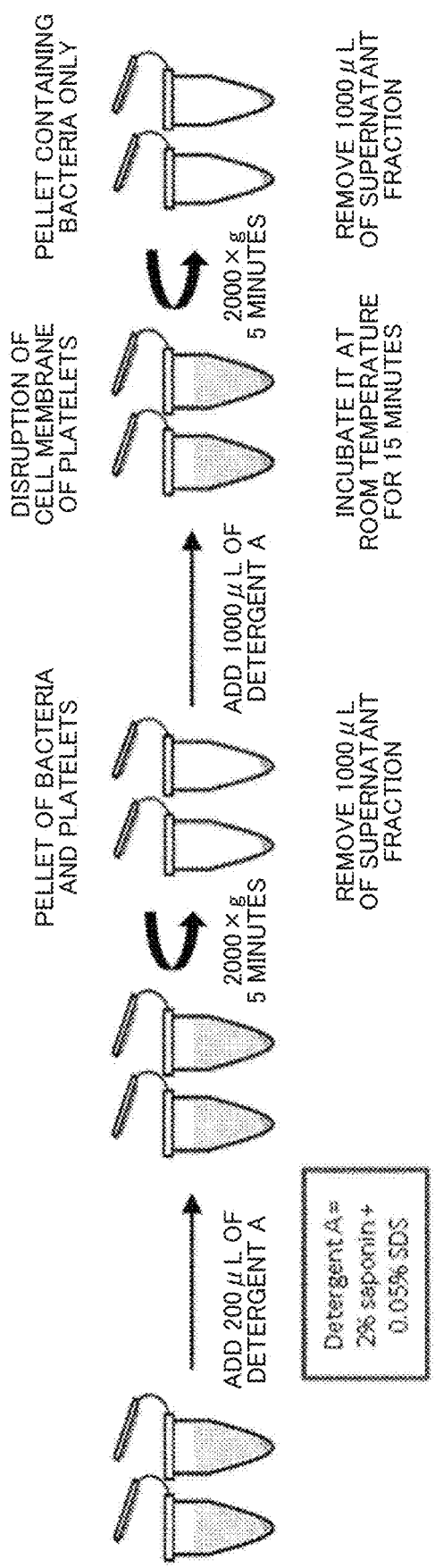
FIG. 4 illustrates operations and an effect of detergent treatment.

The disclosure described below provides many different embodiments and Examples for implementing different features of the presented subject matter. These are, of course, merely examples and are not intended to be limiting. Furthermore, the disclosure may use repeatedly reference numbers and/or letters in various examples. Such repeated use is for the sake of brevity and clarity and does not itself need to be related to various embodiments and/or configurations described. Furthermore, when a first element is described as "connected" or "coupled" to a second element, the description includes not only embodiments in which the first and second elements are directly connected or coupled to each other but also embodiments in which the first and second elements are indirectly connected or coupled to each other with one or more other elements interposed therebetween.

An object of the disclosure is to provide a pretreatment method that allows minimization of human-derived ATP in a blood sample (including a cultured blood sample) and direct recovery of pathogenic microorganisms in a viable state from a blood sample.

The disclosure is a method of pretreating a blood sample for measuring ATP of pathogenic microorganisms in blood, the method comprising: preparing a pellet of platelets and the pathogenic microorganisms from the blood sample; and subjecting the pellet of platelets and the pathogenic microorganism to the following steps (A) to (C) in any order. The order can include one in which more than one step selected from the following steps (A) to (C) is simultaneously performed:

(A) digesting cell membrane proteins of platelets with a protease;
(B) swelling the platelets in a hypotonic solution; and
(C) disrupting cell membranes of the platelets with a detergent solution under a condition of suppressing an effect on pathogenic microorganisms.

As used herein, the phrase "suppressing the effect on pathogenic microorganisms" means that a recovery rate of viable microorganisms is 50% or more on average for main 19 genera of the pathogenic microorganisms responsible for sepsis.

The pellet of platelets and pathogenic microorganisms is prepared by subjecting a blood sample collected into an anticoagulant-containing blood collection tube to centrifugation or contact with a separator to remove red and white blood cells and centrifuging the resulting supernatant.

Examples of the anticoagulant include EDTA.

In the disclosure, the protease used for protease digestion treatment in the step (A) is a protease (divided into an acidic protease, a neutral protease, or an alkaline protease based on its optimum pH) that originates from microorganisms, such as bacteria and fungi, and is utilized for the digestion of animal proteins.

Specifically, examples of the protease include a protease originating from bacteria belonging to the genus *Bacillus* (e.g., a protease commercially available under the trade name of AROASE) and a protease originating from fungi belonging to the genus *Aspergillus* (e.g., a protease commercially available under the trade name of PANCIDASE).

In the disclosure, the hypotonic solution used for swelling treatment in the step (B) is a solution having an osmotic pressure lower than a blood osmotic pressure. The hypotonic solution is not limited to particular solutions and may be any solution that is nontoxic or harmless to bacteria and swells and disrupts human blood cells only. Examples of the hypotonic solution include a hypotonic buffer composed of 4-(2-hydroxyethyl)-1-piperazine ethane sulfonic acid (HEPES), potassium chloride, and magnesium chloride.

In the disclosure, the detergent solution used in the step (C) is a solution containing at least one selected from the group consisting of an anionic detergent ($D_1$) having a linear hydrocarbon, such as a long alkyl group, in a hydrophobic moiety and a detergent ($D_2$) having a cyclic hydrocarbon, such as a steroid nucleus, in a hydrophobic moiety in the structure.

The anionic detergent ($D_1$) may be any detergent of carboxylate type, sulfonate type, or sulfate type and specifically includes sodium dodecyl sulfate (SDS), sodium lauryl sulfate, lithium dodecyl sulfate (LDS), and N-lauroylsarcosine sodium.

The detergents are preferably used alone or in combination.

A concentration of the anionic detergent ($D_1$) in an entire solution is preferably 0.05 wt % or less.

The detergent ($D_2$) is a compound having a cyclic hydrocarbon, such as a steroid nucleus, in the structure and specifically includes saponin, sodium cholate, sodium deoxycholate, 3-[(3-cholamidopropyl)dimethylammonio]-1-propanesulfonate (CHAPS), and 3-[(3-cholamidopropyl)dimethylammonio]-2-hydroxy-1-propanesulfonate (CHAPSO).

The detergent ($D_2$) need not be used but is preferably used alone or in combination.

For the pretreatment method of blood samples according to the disclosure, bacteria are not digested with proteases and are not swollen in a hypotonic solution because bacteria have peptidoglycan walls.

Also, in a treatment with a detergent solution, the peptidoglycan walls protect bacteria from damage.

For these reasons, cell membranes of red and white blood cells contained in very small amounts and platelets are disrupted through a combination of three effects: digestion of cell membrane proteins with a protease, an increase in intracellular pressure and swelling caused by a hypotonic solution, and emulsification of phospholipids with a detergent solution. The cell membrane disruption causes release of human-derived ATP into an extracellular environment, and the human-derived ATP is then minimized via a washing step and other steps, leading to recovery of a pellet containing only pathogenic microorganisms in a viable state.

The treatment allows ATP measurement based on a common method (e.g., luciferase luminescence assay).

As used herein, the phrase "minimizing human-derived ATP" refers to a removal of human-derived ATP to a degree that does not affect ATP measurement in pathogenic microorganisms.

In the disclosure, human-derived ATP can be reduced to about $1/2,500,000$ or less.

Since pathogenic microorganisms can be recovered in a viable state, the viable microorganisms can be subjected to drug susceptibility tests and determination of the presence or absence of viable microorganisms in samples.

According to the disclosure, determination results from the drug susceptibility tests can be obtained in as little as about 6 hours after blood collection. Therefore, it is expected that the pretreatment method of blood samples of the disclosure is helpful in early treatment of sepsis having a great impact on prognosis.

The present embodiments will be described below. It should be noted that the embodiments described below do not unduly limit the contents described in the claims. Not all of the configurations described in the embodiments are essential configuration requirements.

The Examples describe details from blood collection to ATP measurement and drug susceptibility determination.

It should be noted that a sample pretreatment method according to the disclosure is expressed as Bacterial ATP Measurement in Blood (BAMB) Procedure.

The overall flow of steps is shown in FIG. 12.

The steps 2 to 4 may be performed in any order.

The blood samples were whole blood collected from patients with suspected sepsis at Toyama University Hospital and Nagaresugi Geriatric Hospital. All procedures in the Examples described below were performed under approval from the Ethics Committee at the University of Toyama and the Ethics Committee at the Nagaresugi Geriatric Hospital and with written informed consent obtained from all patients. The methods performed in the Examples were carried out in accordance with the approved guidelines.

Example 1

Pretreatment of a blood sample was performed in the order of (A), (B), and (C).

Step 1: Preparing a Pellet of Platelets and Bacteria from a Whole Blood

A "pellet of platelets (including a very small amount of red and white blood cells) and pathogenic microorganisms" is prepared by removing red and white blood cells from a blood sample.

As shown in FIG. 1, blood is collected into, for example, a separator-containing EDTA blood collection tube and gently centrifuged to obtain a supernatant.

The supernatant is transferred to new tubes and strongly centrifuged to obtain pellets of platelets and pathogenic microorganisms.

Specifically, a total of 5 mL of venous blood was collected into a plasma separation EDTA tube (Vacutainer® PPT™ Plasma Preparation Tube, BD Biosciences, CA, USA).

The blood sample was then centrifuged at 1100×g for 10 minutes to spin down blood cells, and the supernatant fraction (2 mL) containing plasma and bacteria was used.

The supernatant was aliquoted into two parts (each 1 mL), centrifuged again at 2000×g for 10 minutes, and then 900 μL of a supernatant fraction was carefully removed so as not to disturb the pellet.

Step 2: Protease Treatment (Digestion of Cell Membrane Proteins of Platelets)

Cell membrane proteins of platelets (and a very small amount of red and white blood cells) are digested.

Bacteria have proteoglycan walls and thus are not digested with a protease.

As shown in FIG. 2, for example, a protease is added and incubated.

Specifically, 1 mL (10% w/v) of a protease (Aroase NP-10: Yakult Pharmaceutical Industry Co., Ltd., Tokyo, Japan) dissolved in molecular biology research-grade distilled water (UtraPure™ DNase/RNase-Free distilled water, Thermo Fisher Scientific, Massachusetts, USA, hereinafter referred to as distilled water) was added to the pellet and pipetted 10 times followed by incubation at 37° C. for 10 minutes.

After incubation, the mixture was centrifuged at 2000×g for 5 minutes, and 1 mL of a supernatant fraction was then carefully removed so as not to disturb the pellet.

Step 3: Treatment with a Hypotonic Solution (Platelet Swelling)

The intracellular pressure of platelets (and a very small amount of red and white blood cells) is raised to induce swelling and facilitate disruption.

Bacteria have peptidoglycan walls and thus are not swollen.

As shown in FIG. 3, the pellets are treated with a hypotonic solution with a low osmotic pressure.

Specifically, HEPES (pH7.9, DOJINDO Molecular Technologies, Tokyo, Japan), KCl (Wako Pure Chemical Industries, Ltd., Tokyo), and $MgCl_2 \cdot 6H_2O$ are dissolved in distilled water to 10 mM, 1.5 mM, and 10 mM, respectively followed by autoclaving to prepare a hypotonic solution, pH 7.9.

Subsequently, 800 μL of the hypotonic solution was added to the pellet and pipetted 10 times followed by incubation at room temperature for 5 minutes.

Step 4: Detergent Treatment

Cell membranes of platelets (and a very small amount of red and white blood cells) are disrupted.

After hypotonic solution treatment, centrifugation is performed for pelletizing microorganisms, but a step of adding a detergent solution to the hypotonic solution before the centrifugation is required to recover bacteria.

For example, *Pseudomonas aeruginosa* is easily adhered to an interior wall of a tube, and therefore when *Pseudomonas aeruginosa* cells are centrifuged without a detergent, most of the cells remain on the interior wall to recover only a few cells.

However, most of other microorganism species have no such problems.

Saponin, a type of detergent having a cyclic hydrocarbon in a hydrophobic moiety acts on the cholesterol of human cell membranes to penetrate like a wedge and weaken (disrupt) the structure of cell membranes.

On the other hand, a bacterial cell wall has a peptidoglycan layer, and thus saponin does not act on bacterial cell walls.

SDS, a type of anionic detergent having a linear hydrocarbon in a hydrophobic moiety emulsifies phospholipids of human cell membranes, which is a lipid bilayer, to disrupt the cell membrane.

SDS can damage bacterial cell walls, but for example, SDS at a concentration decreased to 0.05% does not kill even *Streptococcus agalactiae* cells that are easily killed through detergent treatment.

Treatment with SDS at a concentration as low as 0.05% has a disruption effect mainly on human cell membranes while minimizing effects on bacteria.

The workflow is shown in FIG. 4.

Specifically, after incubation in the step 3, 200 μL of Detergent A, which contains 2% saponin (SERVA Electrophoresis GmbH, Heidelberg, Germany) and 0.05% SDS (Wako Pure Chemical Industries, Ltd.) dissolved in phosphate buffered saline, pH 7.4 (PBS: Thermo Fisher Scientific), was added to a mixture of the hypotonic solution and pellet. The mixture was pipetted 10 times followed by centrifugation at 2,000×g for 5 minutes, and then 1 mL of supernatant fraction was carefully removed so as not to disturb the pellet.

Next, 1 mL of Detergent A was added to the pellet again, and the mixture was pipetted 20 times followed by incubation at room temperature for 15 minutes.

Step 5: Washing Pellet (Pelletizing Viable Microorganisms while Minimizing Human-Derived ATP Background)

Organelles and ATP derived from platelets (and a very small amount of red and white blood cells) are washed away together with Detergent components to recover only pathogenic microorganisms in a viable state.

Figure 5:
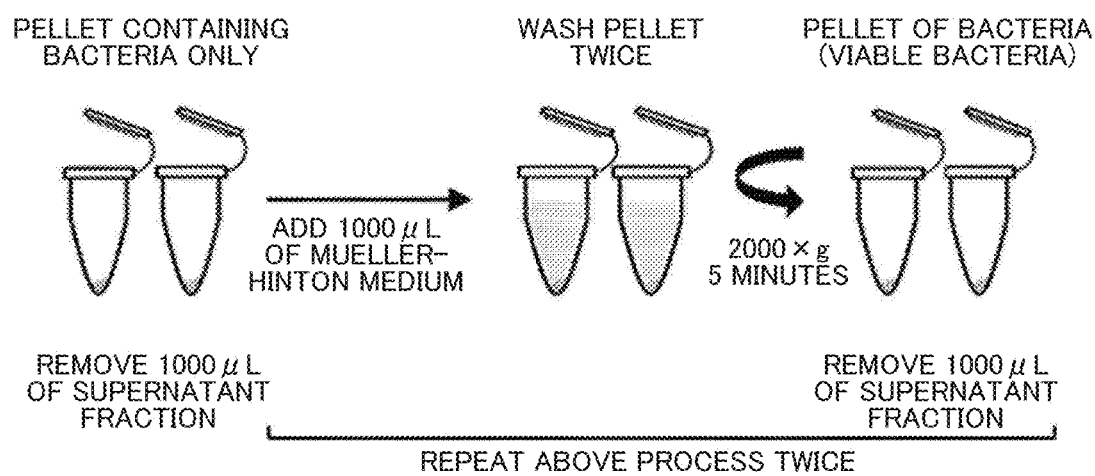
FIG. 5 illustrates operations to wash pellets.

The workflow is shown in FIG. 5.

Specifically, after incubation in the step 4, the mixture was centrifuged at 2000×g for 5 minutes, and then 1 mL of supernatant fraction was carefully removed so as not to disturb the pellet.

Next, 1 mL of Muller-Hinton medium (Muller-Hinton II broth, Cation-adjusted, BD Biosciences) was added to the pellet and gently turned upside down several times followed by centrifugation at 2000×g for 5 minutes again.

After centrifugation, 1 mL of supernatant fraction was carefully removed so as not to disturb the pellet.

Subsequently, the pellet washing step was repeated again.

In other words, 1 mL of Muller-Hinton medium was added to the pellet and gently turned upside down followed by centrifugation at 2000×g for 5 minutes again.

After centrifugation, 1 mL of supernatant fraction was carefully removed so as not to disturb the pellet.

The resulting pellet is a bacterial pellet of pathogenic microorganisms responsible for sepsis in which human-derived ATP background is minimized.

Step 6: Culturing Pathogenic Microorganisms (with/without an Antimicrobial)

Pathogenic microorganisms (viable microorganisms) recovered from a blood sample are cultured with shaking in the presence and absence of an antimicrobial.

Figure 6:
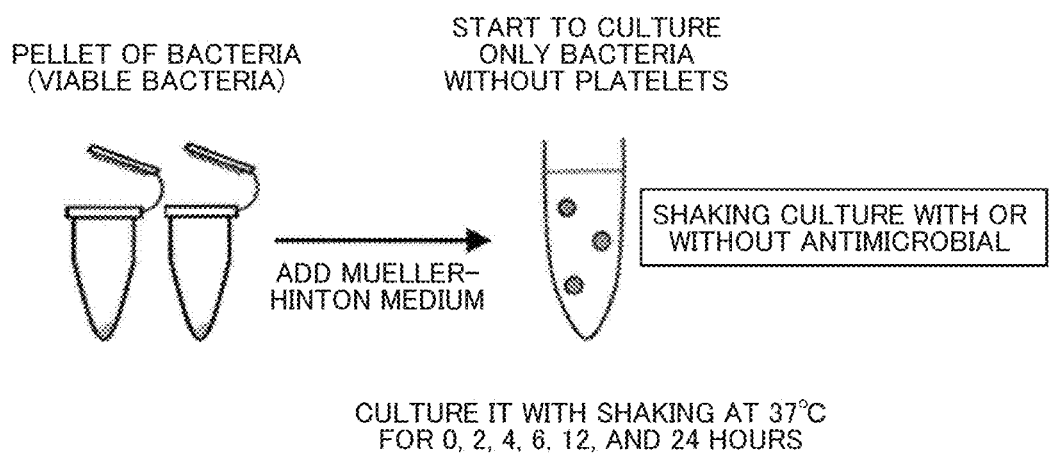
FIG. 6 illustrates operations to culture the recovered pathogenic microorganisms.

An example of the operations is shown in FIG. 6.

Specifically, after BAMB procedure, 1 mL of Muller-Hinton medium was added to the pellet.

The mixture in the two tubes were combined into one mixture and divided into two tubes again to give equal bacterial counts.

Subsequently, shaking culture was performed at 37° C. for 0, 2, 4, 6, 12, and 24 hours in the presence or absence of 2.0 µg/ml Levofloxacin (LVFX)(Sigma-Aldrich, USA).

Step 7: Measurement of ATP in Viable Microorganisms and Determination of Drug Susceptibility after Culturing Pathogenic Microorganisms At various time points after the start of culture, ATP in viable microorganisms is measured to determine drug susceptibility.

Typically, drug susceptibility can be rapidly determined in about 4 hours after the start of culture, that is, about 6 hours (including 2 hours of the pretreatment step) after blood collection.

Figure 7:
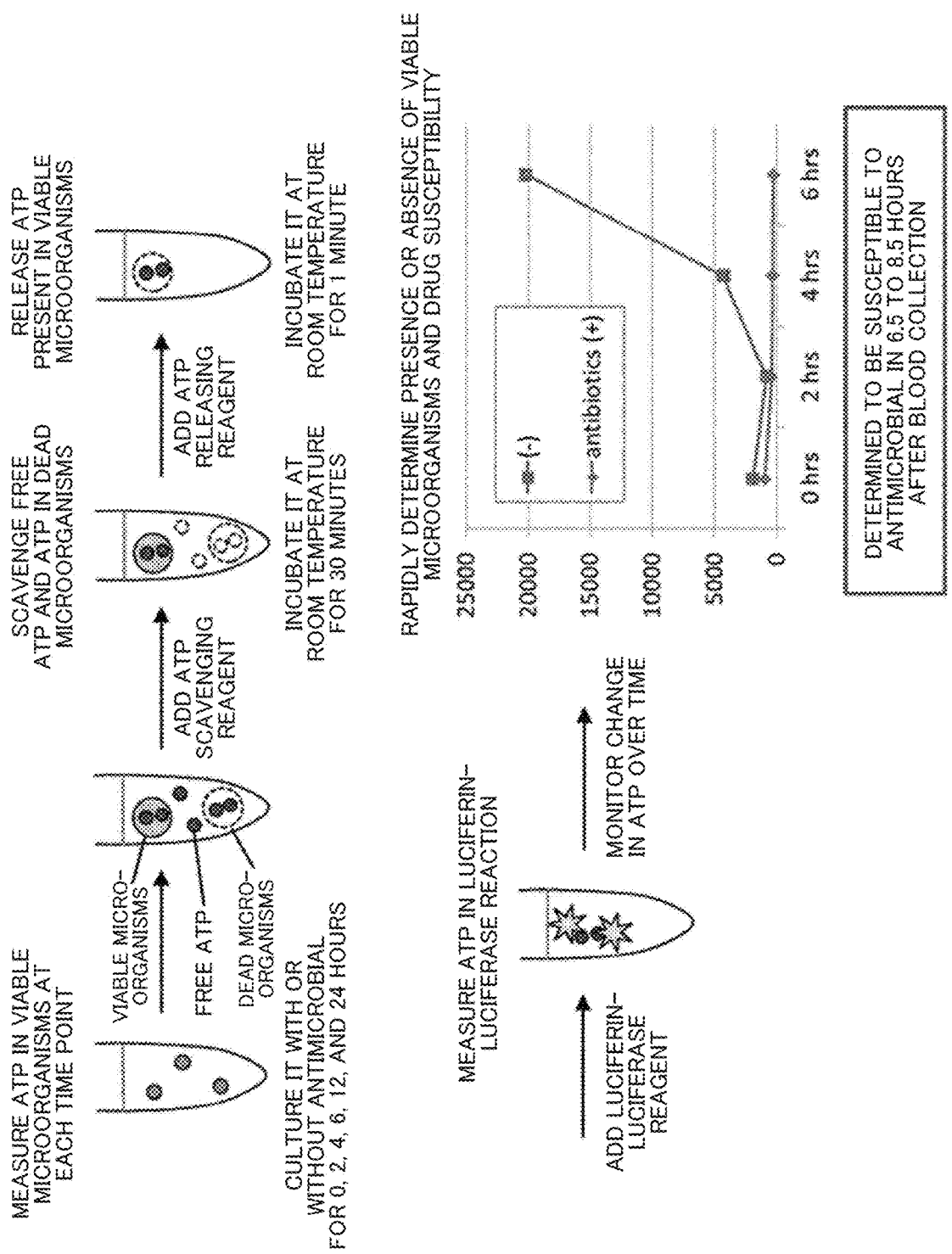
FIG. 7 illustrates an example of ATP measurement and drug susceptibility determination.

An example of the operations is shown in FIG. 7.

Specifically, ATP measurement in viable microorganisms was performed using ATP bioluminescence according to the procedure described below.

It should be noted that an automated ATP bioluminometer was used for ATP measurement.

The automated ATP bioluminometer was a prototype model developed by Hitachi, Ltd. and allowed ATP measurement at the attomole level for detecting a single microorganism.

A CheckLite™ HS Set (Kikkoman Biochemifa, Tokyo, Japan) and an ATP standard sample (Kikkoman Biochemifa) were used as reagents for ATP measurement in viable microorganisms.

The CheckLite™ HS Set includes an ATP-removing reagent, an ATP extraction reagent, and a bioluminescence reagent.

Bacterial samples and ATP standard samples were serially diluted by using distilled water (UltraPure™ DNase/RNase-Free distilled water, Thermo Fisher Scientific) as a washing solution and a buffer for dilution.

Two dilution series for high and low concentration measurements were prepared with an ATP standard sample (Kikkoman Biochemifa) to create an ATP calibration curve.

The dilution series for high concentration measurement was prepared by diluting an ATP standard sample in sterile water to 100 to $2\times10^9$ amol/mL.

The dilution series for low concentration measurement was prepared by diluting an ATP standard sample in sterile water or an ATP extraction reagent to 100 to 500 amol/mL.

Sterile water or an ATP extraction reagent was used as a blank sample.

ATP bioluminescence was measured in the following steps.

First, 10 µL of an ATP standard sample diluted in sterile water or an ATP extraction reagent was added to a reaction tube, and 1 mL of bioluminescence reagent was added to the reagent tube. Each tube was placed in an automated ATP bioluminometer.

Then, 50 µL of bioluminescence reagent was added to the sample by the automated ATP bioluminometer.

Procedures of measurement of intracellular ATP in bacteria

First, ATP-removing reagent was diluted in PBS to 20% (v/v).

Next, 12.5 µL of 20% (v/v) ATP-removing reagent was added to 12.5 µL of a bacterial sample cultured with shaking.

The mixture was incubated for 30 minutes to remove extracellular ATP and ATP from dead microorganisms.

After incubation, 25 µL of the ATP extraction reagent was added to the bacterial sample or a blank sample.

The samples were incubated for 1 minute to extract intracellular ATP in viable microorganisms.

10 µL of the sample subjected to intracellular ATP extraction was added to a reaction tube which was placed in an automated ATP bioluminometer.

Intracellular ATP in viable microorganisms present in the sample was mixed with bioluminescence reagent, and bioluminescence was measured for 30 seconds.

Relative Light Unit (RLU) was calculated as an average of values measured for 5 seconds after reaching the maximum intensity within 30 seconds after mixing the sample with bioluminescence reagent.

ATP bioluminescence (RLU) in the sample was compared with an ATP calibration curve (RLU/amol) to quantify ATP and determine ATP (amol) in whole bacterial cells.

Figure 8A:
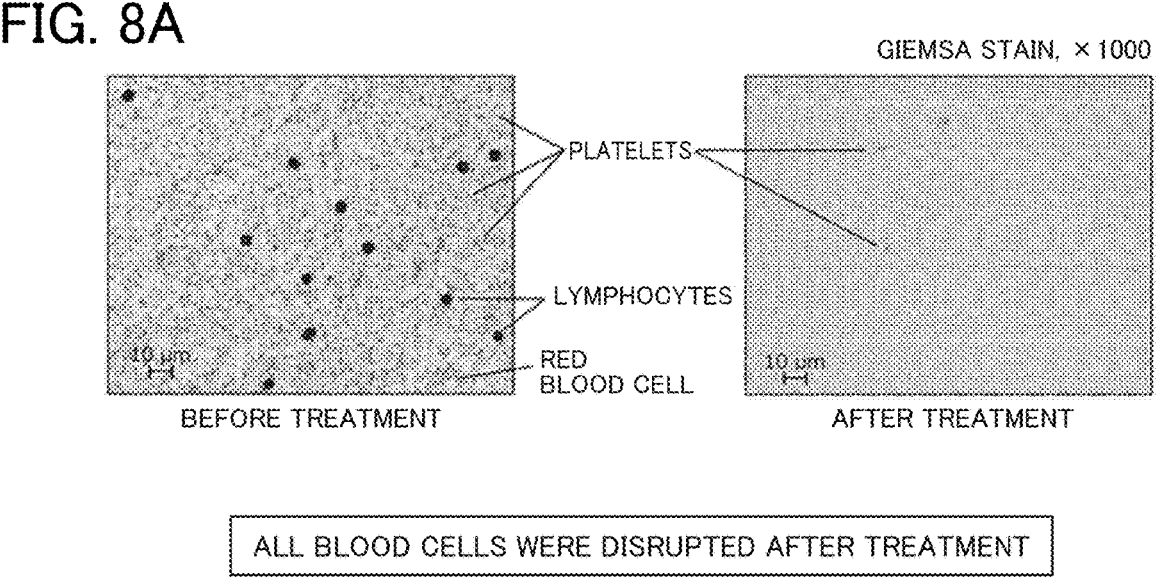
FIGS. 8A and 8B illustrate results of removing human-derived ATP.
Figure 8B:
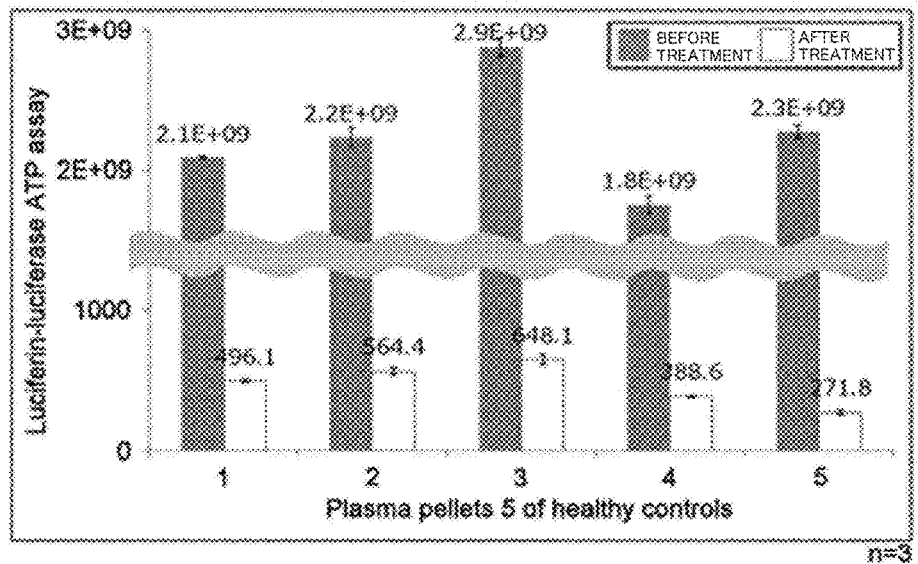

FIGS. 8A and 8B illustrate evaluation results of the ability of removing human-derived ATP.

FIG. 8A represents photomicrographs of plasma pellets before and after the treatment in the process according to the disclosure (BAMB procedure).

It is seen that all blood cells were disrupted and removed after the treatment.

FIG. 8B illustrates results of ATP measurement of plasma pellets before and after the treatment of bloods collected from five healthy subjects.

The graph shows that human-derived ATP was reduced to about 1/2,500,000.

FIG. 9 (Table 1) illustrates recovery results of 19 bacterial genera frequently detected from cultured blood with sepsis.

The recovery rate averaged 93.6% in ATP measurement and 71.9% in CFU measurement.

Figure 10A:
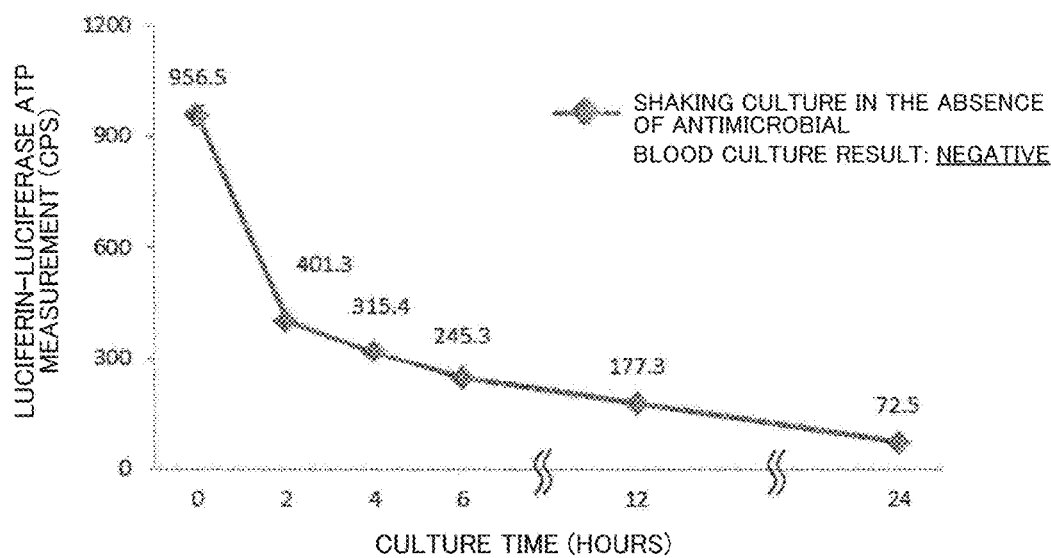
FIG. 10A and FIG. 10B illustrate examples of determining the presence or absence of viable microorganisms in clinical samples.
Figure 10B:
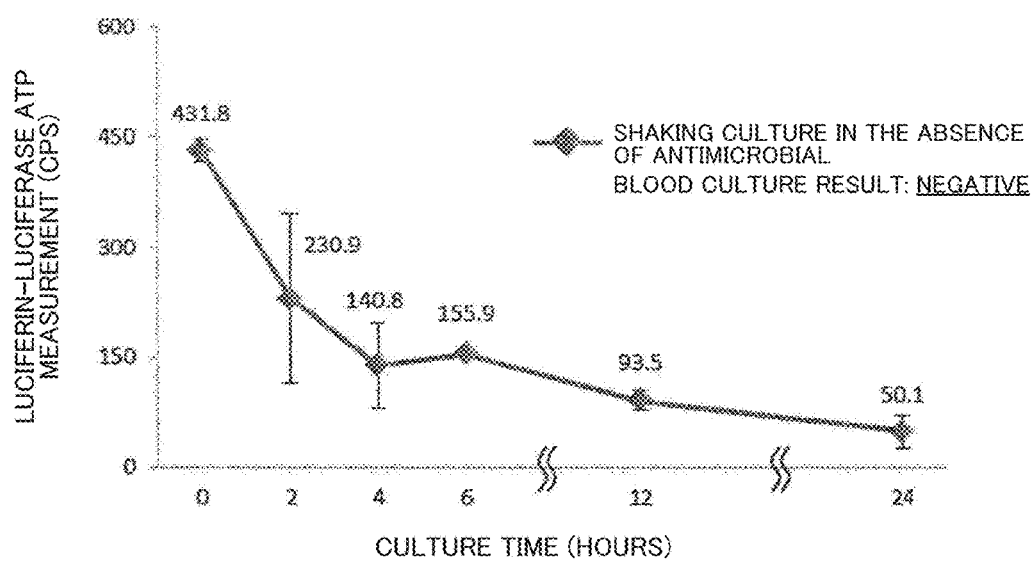
Figure 11C:
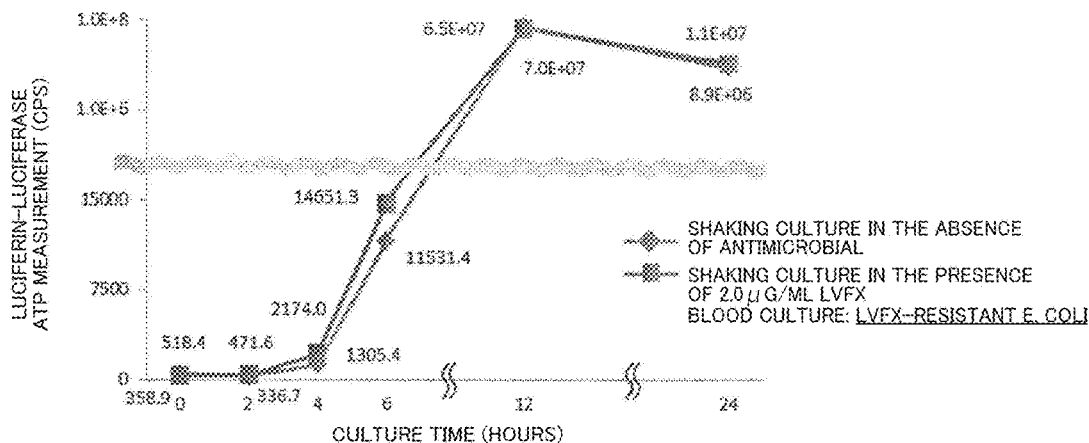
FIG. 11C, FIG. 11D, and FIG. 11E illustrate examples of determining drug susceptibility of clinical samples.
Figure 11D:
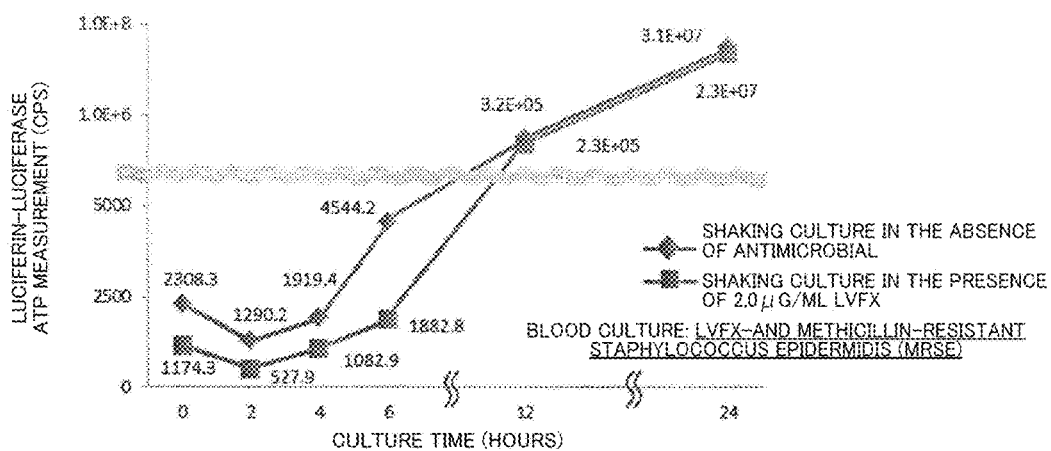
Figure 11E:
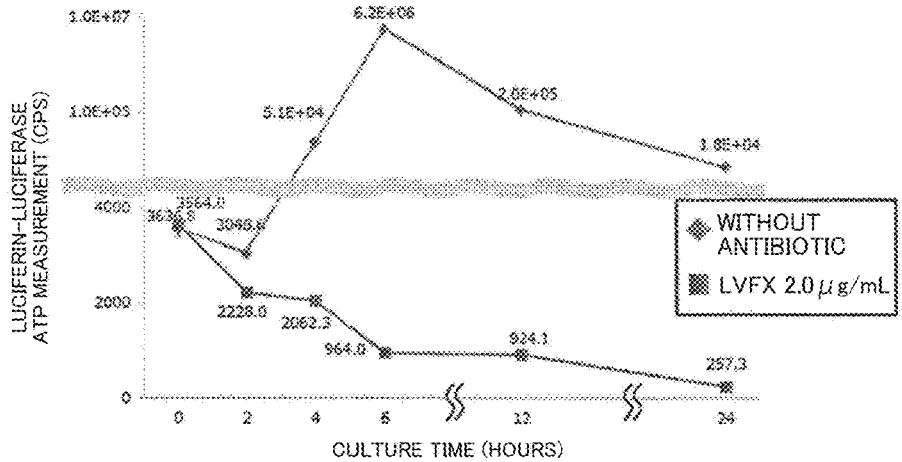

FIG. 10 and FIG. 11 illustrate examples of results from clinical samples subjected to the BAMB procedure according to the disclosure.

Samples (a) and (b) were blood samples from patients with suspected sepsis and represented blood culture-negative examples.

In the period of culture after the BAMB procedure, an increase in ATP was not observed, which revealed that viable microorganisms were not present in the blood.

Samples (c) and (d) were blood samples from patients with sepsis and represented blood culture-positive samples in which E. coli (c) and MRSA (d) resistant to an antimicrobial, levofloxacin (LVFX) were detected.

In 4 hours from the start of culture after the BAMB procedure, an increase in ATP was observed regardless of the presence or absence of LVFX.

In other words, in the ATP measurement, it was determined in 4 hours from the start of culture (in 6 hours after blood collection) that pathogenic microorganisms (viable microorganisms) were present in the blood and were LVFX-resistant microorganisms.

Sample (e) was a blood sample from patients with sepsis and represented blood culture-positive samples in which two bacterial species of *Proteus mirabilis* and *Enterococcus faecalis* susceptible to an antimicrobial, LVFX were detected.

In 4 hours from the start of culture after the BAMB procedure, an increase in ATP was observed in the absence of LVFX, and a decrease in ATP was observed in the presence of LVFX.

In other words, in the ATP measurement, it was determined in 4 hours from the start of culture (in 6 hours after blood collection) that pathogenic microorganisms (viable microorganisms) were present in the blood and were LVFX-susceptible microorganisms.

Example 2

The order of steps 2 to 4 in Example 1 was altered to the order of step 3, 2, and 4, but other steps and other variables were the same as in Example 1. These conditions were used to perform an experiment 3 times.

The results demonstrated that the background value (CPS value at 0 hours in FIG. 10) averaged 476.

Example 3

The order of steps 2 to 4 in Example 1 was altered to the order of step 4, 2, and 3, but other steps and other variables were the same as in Example 1. These conditions were used to perform an experiment 3 times.

The results demonstrated that the background value (CPS value at 0 hours in FIG. 10) averaged 500.

Example 4

The detergent used in step 3 of Example 1 was altered to SDS only, and other steps and other variables were the same as in Example 1. These conditions were used to perform an experiment 3 times.

The results demonstrated that the background value (CPS value at 0 hours in FIG. 10) averaged 479.

Example 5

Procedures of recovering viable microorganisms from a blood culture bottle and performing a rapid drug susceptibility test through ATP measurement This Example describes a method of directly recovering pathogenic microorganisms in a viable state while minimizing ATP background in a blood culture-positive bottle.

Because cell membranes of blood cells that experienced blood culture were easily disrupted, protease treatment in step 2 of Example 1 was unnecessary, and blood cells (including platelets) can be disrupted through only a rapid and simplified pretreatment method using a mixture of a hypotonic solution and Detergent A.

Subsequently, the recovered viable microorganisms were cultured and subjected to a rapid drug susceptibility test through ATP measurement.

The protocol of this Example will be described below.
1. Place 100 μl of a cultured sample (1 hour after it is found to be blood culture-positive) into a 1.5 ml Eppendorf tube.
2. Add 800 μl of a hypotonic solution and 200 μl of Detergent A and pipet it 20 times followed by centrifugation (2000×G, for 10 minutes, at room temperature) to obtain a pellet of microorganisms.
3. Remove 1000 μl of supernatant.
4. Dilute the residue 1:3000 in Muller-Hinton medium.
5. Add 270 μl of the diluted product to each of two 1.5 ml Eppendorf tubes.
6. Add 30 μl of an ATP scavenging reagent to each of the two Eppendorf tubes.
7. Add 33.3 μl of levofloxacin (LVFX, 20 μg/ml) to one Eppendorf tube, and add 33.3 μl of ultrapure water to the other tube. Culture these preparations at 35° C.
8. The time points of measurement are at 2 hours, 4 hours, and 6 hours (24 hours) after the start of culture.
9. Collect 10 μl of the sample per time point at the three time points.
10. Add 10 μl of an ATP extraction reagent and vortex the mixture followed by measurement of the ATP level.

Detergent A is also essential in this protocol (FIG. 13).

As shown in Table 2, the results obtained by culturing bloods from healthy subjects for 4 hours and measuring human-derived ATP background demonstrate that blood cells cannot be sufficiently disrupted in a hypotonic solution+0.05% SDS (without saponin) or in only a hypotonic solution.

Figure 14:
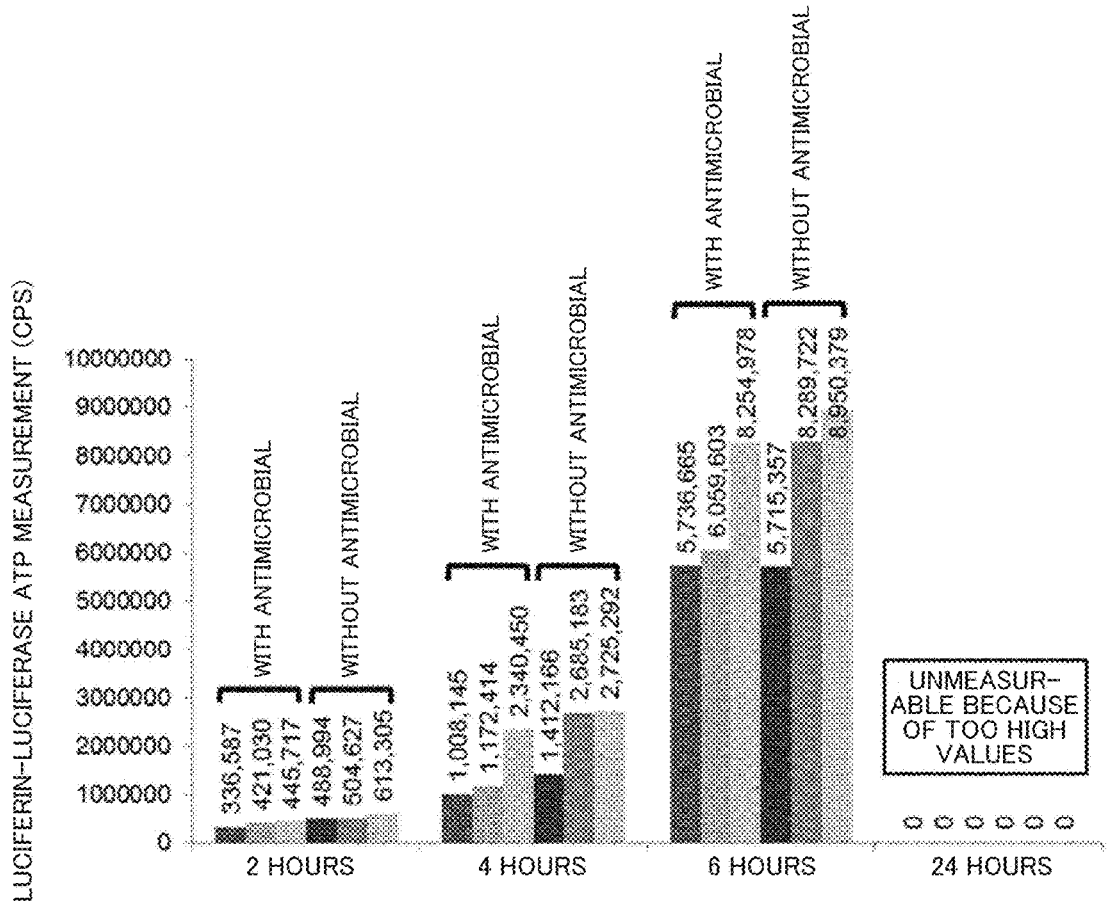
FIG. 14 illustrates an example of determining drug susceptibility of cultured blood samples.

FIG. 14 illustrates results from the rapid drug susceptibility test in this Example.

As culture time proceeded, microbial ATP levels increased regardless of the presence or absence of the antimicrobial. It was proved 4 hours after the start of culture that the microorganisms were resistant to the antimicrobial (levofloxacin).

In fact, levofloxacin-resistant *Escherichia coli* was detected in a conventional test, and this result of drug susceptibility was consistent with the results in this Example.

Thus, it was possible to obtain correct susceptibility results in as little as 4 hours after becoming blood culture-positive.

Example 6

Case 2 of the rapid drug susceptibility test through ATP measurement from a blood culture bottle According to the same protocol as in Example 5 (except that a cultured sample at 4 hours after becoming blood culture-positive was used), a rapid drug susceptibility test was performed from a blood culture bottle in which blood from a patient with sepsis different from the patient in Example 5 was cultured.

FIG. 15 illustrates results of the rapid drug susceptibility test in this Example.

As culture time proceeded, microbial ATP levels increased in the absence of the antimicrobial, and microbial ATP levels decreased in the presence of the antimicrobial (levofloxacin).

In other words, it is revealed 4 hours after the start of culture that the microorganisms are susceptible to the antimicrobial (levofloxacin).

In fact, levofloxacin-susceptible *Streptococcus anginosus* was detected in a conventional test, and this result of drug susceptibility was consistent with the result in this Example.

Thus, it was possible to obtain correct susceptibility results in as little as 4 hours after becoming blood culture-positive.

Example 7

Case 3 of the rapid drug susceptibility test through ATP measurement from a blood culture bottle According to the same protocol as in Example 5 (except that a cultured sample at 5 hours after becoming blood culture-positive was used), a rapid drug susceptibility test was performed from a blood culture bottle in which blood from a patient with sepsis different from the patients in Examples 5 and 6 was cultured.

Figure 16:
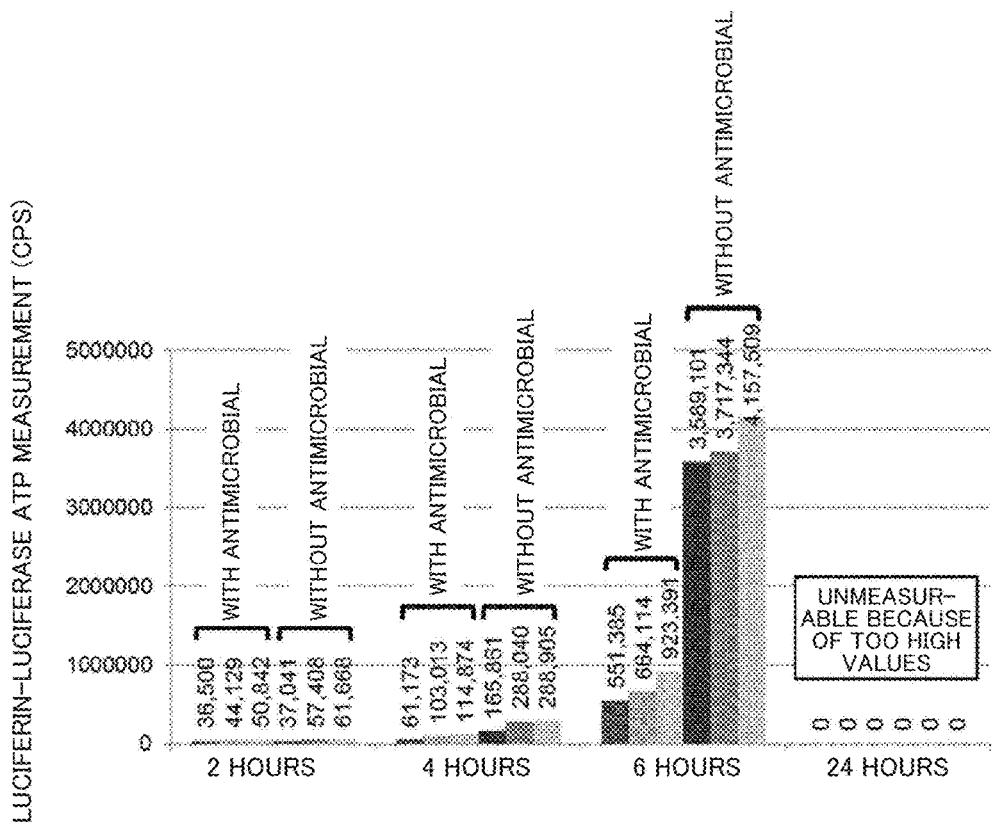
FIG. 16 illustrate an example of determining drug susceptibility of cultured blood samples.

FIG. 16 illustrates results of the rapid drug susceptibility test in this Example.

As culture time proceeded, microbial ATP levels increased regardless of the presence or absence of the antimicrobial. It was proved 4 to 6 hours after the start of culture that the microorganisms were resistant to the antimicrobial (levofloxacin).

However, since increases in microbial ATP levels have a difference between the presence and absence of the antimicrobial, it is likely that antimicrobial-resistant microorganisms and antimicrobial-susceptible microorganisms were mixed. Levofloxacin-resistant *Staphylococcus capitis* or *Staphylococcus caprae* was detected in a conventional test, and this result of drug susceptibility was consistent with the result in this Example.

Thus, it was possible to obtain correct susceptibility results in as little as 4 to 6 hours after becoming blood culture-positive.

The pretreatment method of blood samples according to the disclosure can be utilized for rapid drug susceptibility tests through ATP measurement in blood samples from patients with suspected sepsis.

The pretreatment method of blood samples according to the disclosure can be utilized for rapid determination (that can compensate for shortcomings of genetic tests) of the presence or absence of viable microorganisms in blood samples, through ATP measurement.

The pretreatment method of blood samples according to the disclosure can be utilized for rapid drug susceptibility tests through ATP measurement in cultured blood samples from blood culture bottles.

The pretreatment method of blood samples according to the disclosure can be utilized for rapid determination of the presence or absence of viable microorganisms, rapid drug susceptibility tests, and the like, in cerebrospinal fluid (bacterial meningitis), pericardial fluid (pericarditis), pleural fluid (pleuritis), peritoneal fluid (peritonitis), fluid in the joint capsule (orthopedic postoperative infection), aqueous humor (endophthalmitis), lung lavage fluid (pneumonia), urine (urinary tract infection), postoperative drainage (postoperative infection), CV catheter tip (sepsis caused by biofilm at the catheter tip in long-term bedridden patients), and the like, in addition of blood samples.

Although the Examples of the disclosure are described above in detail, those skilled in the art would easily understand that many modifications can be made without substantially departing from novel matters and effects of the disclosure. Therefore, such modifications shall be all included in the scope of the disclosure.

What is claimed is:

1. A method of pretreating a blood sample for measuring ATP of a pathogenic microorganism in blood, comprising:
   preparing a pellet of platelets and the pathogenic microorganism from the blood sample; and
   subjecting the pellet of platelets and the pathogenic microorganism to the following steps (A) to (C) in any order:
   (A) digesting cell membrane proteins of platelets with a protease;
   (B) swelling the platelets in a hypotonic solution; and
   (C) disrupting cell membranes of the platelets with a detergent solution,
   wherein the pellet of platelets and the pathogenic microorganism is prepared by subjecting a blood sample collected into an anticoagulant-containing blood collection tube to centrifugation or contact with a separator to remove red and white blood cells and centrifuging the resulting supernatant,
   wherein the detergent solution used in the step (C) comprises an anionic detergent ($D_1$) having a linear hydrocarbon in a hydrophobic moiety, and
   wherein the anionic detergent ($D_1$) comprises saponin and 0.05 wt % sodium dodecyl sulfate (SDS).

2. The method of pretreating a blood sample according to claim 1, wherein more than one step selected from the steps (A) to (C) is simultaneously performed.

3. The method of pretreating a blood sample according to claim 1, wherein the protease used for protease digestion treatment in the step (A) is a protease originating from a microorganism.

4. The method of pretreating a blood sample according to claim 1, wherein the hypotonic solution used in the step (B) is a solution having an osmotic pressure lower than a blood osmotic pressure.

* * * * *